United States Patent
Rastrelli et al.

(10) Patent No.: US 11,426,337 B2
(45) Date of Patent: Aug. 30, 2022

(54) ANTIPERSPIRANT AND DEODORANT COMPOSITIONS

(71) Applicant: KALICHEM SRL, Rezzato (IT)

(72) Inventors: Gianbattista Rastrelli, Rezzato (IT); Francesco Rastrelli, Rezzato (IT)

(73) Assignee: KALICHEM SRL, Rezzato (IT)

( * ) Notice: Subject to any disclaimer, the term of this patent is extended or adjusted under 35 U.S.C. 154(b) by 0 days.

(21) Appl. No.: 17/598,455

(22) PCT Filed: Mar. 27, 2020

(86) PCT No.: PCT/EP2020/058742
§ 371 (c)(1),
(2) Date: Sep. 27, 2021

(87) PCT Pub. No.: WO2020/201103
PCT Pub. Date: Oct. 8, 2020

(65) Prior Publication Data
US 2022/0142883 A1    May 12, 2022

(30) Foreign Application Priority Data

Mar. 29, 2019  (IT) .................. 102019000004805

(51) Int. Cl.
*A61K 8/29* (2006.01)
*A61K 8/28* (2006.01)
*A61Q 15/00* (2006.01)
*A61K 8/19* (2006.01)
*A61K 8/26* (2006.01)
*A61K 8/27* (2006.01)

(52) U.S. Cl.
CPC .................. *A61K 8/29* (2013.01); *A61K 8/19* (2013.01); *A61K 8/26* (2013.01); *A61K 8/27* (2013.01); *A61K 8/28* (2013.01); *A61Q 15/00* (2013.01)

(58) Field of Classification Search
CPC .......... A61K 7/32; B01J 27/18; B01J 27/1817
USPC ........................................ 424/65, 66, 67, 68
See application file for complete search history.

(56) References Cited

U.S. PATENT DOCUMENTS

| | | | |
|---|---|---|---|
| 2,854,382 A | 9/1858 | Grad | |
| 2,814,585 A | 11/1957 | Erdmann | |
| 4,871,525 A | 10/1989 | Giovanniello et al. | |
| 5,122,418 A * | 6/1992 | Nakane | A61Q 19/00 424/47 |
| 5,223,244 A * | 6/1993 | Moro | A61K 8/046 424/45 |
| 2006/0045860 A1 | 3/2006 | Gupta | |
| 2014/0287913 A1* | 9/2014 | Tsukada | B01J 27/1817 502/208 |

FOREIGN PATENT DOCUMENTS

| | | |
|---|---|---|
| FR | 2812194 A1 | 2/2002 |
| JP | S62135411 B2 | 6/1987 |
| JP | H05309266 B | 11/1993 |
| JP | H10118167 B | 5/1998 |
| JP | 2000219505 A | 8/2000 |
| WO | 2002034223 A2 | 5/2002 |
| WO | 2020201103 A1 | 10/2020 |

OTHER PUBLICATIONS

D. Gopi et al. "Synthesis and Spectral Characterization of Silver/ Magnesium Co-Substituted Hydroxyapatite For Biomedical Applications", Spectrochimica Acta. Part A: Molecular and Biomolecular Spectroscopy, vol. 127, Jun. 1, 2014 (Jun. 1, 2014), pp. 286-291, XP055646684, NL; ISSN: 1386-1425, DOI: 10.1016/j.saa.2014.02. 057 p. 288, left-hand column, paragraph 2; p. 290, left column, last paragraph—right-hand column, paragraph 1:, figures S2(d), S6.
Rajendran Abinaya et al: "Multi-element substituted hydroxyapatites: synthesis structural characteristics and evaluation of their bioactivity, cell viability, and antibacterial activity", Journal of Sol-Gel Science and Technology, Springer, New York, NY, US, vol. 86, No. 2, Mar. 26, 2018 (Mar. 25, 2018), pp. 441-458, XP036489847, ISSN: 0928-0707, DOI: 10.1007/S10971-018-4634-X [retrieved on Mar. 26, 2018] p. 443-p. 444; figures 6-8.
Hiroshi Nishida et al: "Malodors adsorption behavior of metal cation incorporated hydroxyapatite", Journal of Environmental Chemical Engineering, vol. 5, No. 3, Jun. 1, 2017 (Jun. 1, 2017), pp. 2815-2819, XP055646707, ISSN: 2213-3437, DOI: 10.1016/jece. 2017.05.040 cited in the application; the whole document.
D. F. Swaile, et al, "Clinical Studies of sweat rate reduction by an over-the-counter soft solid antiperspirant and comparison with a prescription antiperspirant product in male panelists", British Journal of Dermatology, 2012, 166 (Suppl. 1), pp. 22-26.
R. Caputo, et al. "Manuale di Dermocosmetologia medica", Raffaello Cortina Editore, 1999, p. 146.
H. Nishida et al. "Malodors adsorption behavior of metal cation incorporated hydroxyapatite", Journal of Environmental Chemical Engineering, 5 (2017), 2815-2819.
Written Opinion of the international Search Authority for PCT/ EP2020/058742 dated Jun. 6, 2020.
International Search Report for PCT/EP2020/058742 dated Jun. 6, 2020.

\* cited by examiner

*Primary Examiner* — Walter E Webb
(74) *Attorney, Agent, or Firm* — Vorys, Sater, Seymour and Pease LLP

(57) ABSTRACT

An antiperspirant and deodorant composition comprising a hydroxyapatite multi-substituted with at least two cations selected among aluminium, zinc, magnesium, zirconium, titanium, copper, silver or iron.

17 Claims, No Drawings

ANTIPERSPIRANT AND DEODORANT COMPOSITIONS

FIELD OF THE INVENTION

The present invention relates to an antiperspirant and deodorant composition comprising a hydroxyapatite multi-substituted with at least two cations selected among aluminium, zinc, magnesium, zirconium, titanium, copper, silver or iron

BACKGROUND OF THE INVENTION

Sweating is a physiological process that occurs to disperse heat both in hot areas and during exercise: on one hand it absolves important physiological functions, while on the other the sweat is the substrate for the formation of odors in the human body. Sweat is the product of sweat glands and is odorless per se; however, the components of the sweat are metabolized by the microorganisms present on the human skin, with the consequent production of volatile compounds which are responsible for unpleasant odors.

Personal care products suitable for controlling sweating are divided into deodorants (that mask the malodors caused by sweat) and antiperspirants (which inhibit/suppress sweating, acting directly on the sweat glands). Deodorants can act as bacteriostatic agents (substances that limit the proliferation of bacterial flora responsible for unpleasant odors without altering the skin microbiota) and/or adsorbents compounds that form complexes with the molecules responsible for odors, reducing their volatility and therefore limiting their diffusion.

Commonly used deodorizing agents are based on zinc salts, in particular zinc carboxylates. They act to exert a malodour-counteracting or eliminating effect by interacting or reacting chemically with malodorous molecules.

Conventional antiperspirant products typically use aluminium-based salts as the active ingredients to control perspiration and malodour. The most frequently used antiperspirant aluminium salts include aluminium chloride and aluminium chlorohydrate. The antiperspirant action is achieved by diffusion of the soluble and acid aluminium salts into the sweat duct. The reaction with sweat takes place at or below the natural physiological pH of the skin surface and produces a gelatinous and insoluble aluminium hydroxide gel that partially blocks the orifices of the sweat glands, whereby the flow of sweat is reduced to a certain degree although not eliminated completely. Furthermore the aluminium salts have astringent effects on skin, tightening the sweat glands which are further narrowed.

Mixed aluminum and zirconium antiperspirant salts have also been known for many years (see, for example U.S. Pat. Nos. 2,814,585, 2,854,382, 4,871,525, WO 2002/034223)

In recent years the safety of chlorohydrate salts used as antiperspirants has been questioned, since the application of chlorohydrate salts may lead to skin irritation (stinging, burning and erythema). In particular, skin irritation is caused by the hyper-acidification of the skin, as a result of the formation of hydrochloric acid due to the interaction of aluminium salts (such as aluminium chloride and aluminium chlorohydrate) with water present in the sweat (see for example D. F. Swaile, L. T. Elstun and K. W. Benzing, "Clinical studies of sweat rate reduction by an over-the counter soft-solid antiperspirant and comparison with a prescription antiperspirant product in male panelists", British Journal of Dermatology, 2012, 166 (Suppl. 1), pp 22-26 or R. Caputo, M. Monti, "Manuale di dermocosmetologia medica", Raffaello Cortina Editore, 1999, p. 146).

The astringent properties of other metal salts, such as titanium, magnesium and zinc salts, makes them candidates for the at least partial substitution of noxious antiperspirant salts, but their effectiveness is actually limited.

Switching to the deodorant actives of cosmetic compositions, zinc salts, hydroxyapatite, magnesium aluminium silicate and other salts are known to have deodorant effect (by way of example see, for hydroxyapatite, JPS62135411 and JPH05309266).

JPH10118167 discloses the use of mono- or multi-substituted hydroaxyapatite with various metal cations as deodorants in air freshener compositions.

The use of mono-substituted hydroaxyapatite with various metal cations for air malodours absorption is disclosed also by H. Nishida, M. Kimata, T. Ogata, T. Kawai, "Malodors adsorption behavior of metal cation incorporated hydroxyapatite", Journal of Environmental Chemical Engineering, 5 (2017), 2815-2819.

JP2000219505 relates to cosmetic antiperspirant compositions containing composite particles of aluminium hydrochloride and amorphous hydroxyapatite.

Various other physical associations of hydroxyapatite with common antiperspirant salts are described in the patent literature; unfortunately, in the physically associated forms, the antiperspirant salt suffers from the drawbacks that have been presented above.

Therefore, a need exists in the art to deliver in a safe manner or to substitute the irritating ions which are commonly used in antiperspirant/deodorant compositions.

It has now been found that multi-substituted hydroxyapatite in which the calcium ions are partially substituted by at least two kind of cations selected among aluminium, zinc, magnesium, zirconium, titanium, copper, silver or iron (here referred to as "multi-substituted hydroxyapatite") can be used to prepare improved antiperspirant and deodorant compositions, thus eliminating or mitigating the adverse effects on skin irritation associated to the commonly used antiperspirant salts.

SUMMARY OF THE INVENTION

It is therefore an object of the present invention a cosmetic composition with antiperspirant and deodorant properties comprising from 0.05 to 35% by weight (wt %) of a multi-substituted hydroxyapatite with at least two cations selected among aluminium, zinc, magnesium, zirconium, titanium, copper, silver or iron.

It is a further object of the invention a cosmetic method for reduction of perspiration of a body and/or reduction of a body odor released by the perspiration, wherein the method comprises applying on the skin a cosmetic composition with antiperspirant and deodorant properties comprising from 0.05 to 35% by weight of a multi-substituted hydroxyapatite with at least two cations selected among aluminium, zinc, magnesium, zirconium, titanium, copper, silver or iron.

DETAILED DESCRIPTION OF THE INVENTION

The use of hydroxyapatite as intimate carrier for aluminium, magnesium, zinc, zirconium, titanium, copper, silver and iron cations is particularly advantageous, because thanks to the slow hydroxyapatite solubilisation rate under the action of the acidic pH of the skin it is possible to achieve a controlled release of zinc, magnesium, aluminium, zirconium, titanium, copper, silver and iron cations during time, thus reducing the number of applications of the product.

The multi-substituted hydroxyapatite of the invention allows obtaining antiperspirant and deodorant compositions that are skin-friendly, long acting, non-irritant and not dangerous for the cutaneous microbiota.

In addition, the multi-substitution of hydroxyapatite with the at least two different metal cations is supposed to result in an improved effect respect to the physical association of hydroxyapatite with other inorganic salts, in terms of perspiration, increased malodour adsorption and increased bacteriostatic activity.

Preferably, the cosmetic composition with antiperspirant and deodorant properties comprises from 0.5 to 25% by weight (wt %) of a multi-substituted hydroxyapatite with at least two cations selected among aluminium, zinc, magnesium, zirconium, titanium, copper, silver or iron.

Accordingly, the cosmetic method for reduction of perspiration of a body and/or reduction of a body odor released by the perspiration preferably comprises applying on the skin a cosmetic composition with antiperspirant and deodorant properties comprising from 0.5 to 25% by weight of a multi-substituted hydroxyapatite with at least two cations selected among aluminium, zinc, magnesium, zirconium, titanium, copper, silver or iron.

Hydroxyapatite is a compound present in the human body, being the main mineral constituent of bone tissue. Indeed, 99% of the calcium in the human body is stored in bone tissue in the form of hydroxyapatite. Hydroxyapatite is a calcium phosphate hydroxide which in nature constitutes 60-70% of bone and 98% of enamel. Its chemical composition is commonly denoted as $Ca_5(PO_4)_3(OH)$, therefore belonging to the apatite group and containing an OH group. The calcium can be present in nature in the said chemical form $Ca_5(PO_4)_3(OH)$, also denoted as $Ca_{10}(PO_4)_6(OH)_2$ to indicate that the elemental cell is formed of two molecules. For the purposes of the present invention, the term "hydroxyapatite" also encompasses, in addition to the previously mentioned, all polymorphic forms, relative hydrates and solvates, in all ratios between phosphate ions, hydroxyl ions and calcium.

In general, multi-substituted (or doped) hydroxyapatite can be obtained thanks to the partial incorporation into the hydroxyaptite structure of anions (by replacing the OH groups) or cations (by replacing calcium cations, $Ca^{2+}$). Various metal cations can be incorporated into the hydroxyapatite structure, such as aluminium ($Al^{3+}$), iron ($Fe^{3+}$ and $Fe^{2+}$), cobalt ($Co^{2+}$), nickel ($Ni^{2+}$), copper ($Cu^{2+}$), silver ($Ag^{2+}$), zinc ($Zn^{2+}$) or magnesium ($Mg^{2+}$). The OH groups can be replaced by anions or anionic groups such as carbonates ($CO_3^{2-}$), silicates, fluoride ions ($F^-$) or chloride ions ($Cl^-$).

The multi-substituted hydroxyapatite of the invention is a hydroxyapatite multi-substituted with at least two cations selected among aluminium, zinc, magnesium, zirconium, titanium, copper, silver or iron. Optionally, said multi-substituted hydroxyapatite can also contain carbonates and silicates.

According to a preferred embodiment, the multi-substituted hydroxyapatite of the invention is a multi-substituted hydroxyapatite with at least two cations selected among aluminium, zinc or magnesium.

According to a more preferred embodiment, the multi-substituted hydroxyapatite of the invention is a multi-substituted hydroxyapatite with aluminium and zinc, a multi-substituted hydroxyapatite with zinc and magnesium or a multi-substituted hydroxyapatite with aluminium and magnesium.

The most preferred multi-substituted hydroxyapatite of the invention is a multi-substituted hydroxyapatite with aluminium and zinc.

Advantageously, the multi-substituted hydroxyapatite with aluminium and zinc comprises $Zn^{2+}$ ions in a molar ratio Zn/Ca of from 0.002 to 0.35 (i.e., from 0.2% to 35%), preferably from 0.05 to 0.25 (i.e., from 5 to 25%) and $Al^{3+}$ ions in a molar ratio Al/Ca of from 0.002 to 0.50 (i.e., from 0.2% to 50%), preferably from 0.05 to 0.35 (i.e., from 5 to 35%).

Advantageously, the multi-substituted hydroxyapatite with magnesium and zinc comprises $Mg^{2+}$ ions in a molar ratio Mg/Ca of from 0.002 to 0.35 (i.e., from 0.2% to 35%), preferably from 0.05 to 0.25 (i.e., from 5 to 25%) and $Zn^{2+}$ ions in a molar ratio Zn/Ca of from 0.002 to 0.35 (i.e., from 0.2% to 35%), preferably from 0.05 to 0.25 (i.e., from 5 to 25%).

Advantageously, the multi-substituted hydroxyapatite with aluminium and magnesium comprises $Al^{3+}$ ions in a molar ratio Al/Ca of from 0.002 to 0.50 (i.e., from 0.2% to 50%), preferably from 0.05 to 0.35 (i.e., from 5 to 35%) and $Mg^{2+}$ ions in a molar ratio Mg/Ca of from 0.002 to 0.35 (i.e., from 0.2% to 35%), preferably from 0.05 to 0.25 (i.e., from 5 to 25%).

The multi-substituted hydroxyapatite with at least two cations selected among aluminium, zinc, magnesium, zirconium, titanium, copper, silver or iron can be obtained by any known process of preparation of substituted hydroxyapatite (such as, for example, dry solid phase reaction, wet precipitation reaction, wet hydrolysis or hydrothermal hydrolysis), by a contacting a source of calcium cations with a source of phosphate anions, in the presence of suitable sources of zinc, aluminium, magnesium, zirconium, titanium, copper, silver or iron cations.

Suitable sources of phosphate anions are disodium hydrogen phosphate, sodium dihydrogen phosphate, orthophosphoric acid, dipotassium hydrogen phosphate, potassium dihydrogen phosphate, di-ammonium hydrogen phosphate or combinations thereof. Preferably, the source of phosphate anions is orthophosphoric acid ($H_3PO_4$).

In the process for preparing the multi-substituted hydroxyapatite, $H_3PO_4$ is used at an initial concentration of from 5 to 1000 g/l, preferably from 50 to 400 g/l.

Suitable sources of calcium cations are calcium fluoride, calcium chloride, calcium nitrate, calcium carbonate, calcium hydroxide, calcium phosphate, calcium acetate, or combinations thereof. Preferably, the source of calcium cations is calcium hydroxide ($Ca(OH)_2$).

In the process for preparing the multi-substituted hydroxyapatite, $Ca(OH)_2$ is used at an initial concentration from 10 to 1000 g/l, preferably from 30 to 400 g/l.

In the embodiments where the multi-substituted hydroxyapatite is a hydroxyapatite multi-substituted with zinc, suitable sources of zinc cations are zinc acetate, zinc nitrate, zinc citrate, zinc fluoride, zinc chloride, zinc hydroxide, zinc carbonate or combinations thereof. Preferably, the source of zinc cations is zinc carbonate ($ZnCO_3$).

In the process for preparing the multi-substituted hydroxyapatite, $ZnCO_3$ is used at an initial concentration from 1 to 600 g/l, preferably from 10 to 150 g/l.

In the embodiments where the multi-substituted hydroxyapatite is a hydroxyapatite multi-substituted with aluminium, suitable sources of aluminium cations are aluminium chloride, aluminium hydrochloride, aluminium sulphate, aluminium nitrate or mixtures thereof. Preferably, the source of aluminium cations is aluminium chloride (AlCl$_3$·6H$_2$O).

In the process for preparing the multi-substituted hydroxyapatite, AlCl$_3$·6H$_2$O is used at an initial concentration from 5 to 100 g/l, preferably from 25 to 700 g/l.

In the embodiments where the multi-substituted hydroxyapatite is a hydroxyapatite multi-substituted with magnesium, suitable sources of magnesium cations are magnesium hydrogen phosphate, trimagnesium phosphate, magnesium dihydrogen phosphate, magnesium chloride, magnesium chloride hexahydrate, magnesium glycerophosphate, magnesium hydroxide, magnesium hydroxide carbonate, magnesium oxide (MgO), magnesium citrate, magnesium silicate or mixtures thereof.

Preferably the source of magnesium cations is magnesium chloride hexahydrate (MgCl$_2$·6H$_2$O).

In the process for preparing the multi-substituted hydroxyapatite, MgCl$_2$·6H$_2$O is used at an initial concentration from 1 to 600 g/l, preferably from 10 to 150 g/l.

Preferably, the process for preparing the multi-substituted hydroxyapatites with aluminium, and zinc and/or magnesium includes the steps of i) preparing a basic aqueous suspension a) of Ca(OH)$_2$, comprising a convenient amount of zinc cations (Zn$^{2+}$) and/or magnesium cations (Mg$^{2+}$), ii) simultaneously adding an aqueous solution b) of H$_3$PO$_4$ and a solution c) of AlCl$_3$·6 H$_2$O to the basic solution prepared in step i).

The addition of solutions b) and c) is carried out at a temperature from 20° C. to 60° C.; preferably from 30° C. to 50° C.

After dripping the solutions b) and c) into the suspension of calcium hydroxide, added with Zn$^{2+}$ and/or Mg$^{2+}$ cations, the resulting mixture is left under stirring for 1 h and then to rest for 24 h. The mother liquor is then removed, for instance by centrifugation. The solid part is preferably redispersed in distilled water and then centrifuged again. This washing operation can be repeated several times, if desired. At the end of it, the powder is dried (for instance by freeze-drying or drying in a ventilated oven at 40-90° C.) and reduced to the desired granulometry for the following uses.

The deodorant and antiperspirant composition of the invention may be available in the solid form or as a suspension, a cream or a liquid. Different ways of application also correspond to the different forms. A stick is used for products available in the solid form, while the roll-on is the most common application mode when the product is available as a suspension or a cream. Aerosol, vaporizers or spray dispensers are used when the products are in the liquid form.

The deodorant and antiperspirant composition may further comprise liquid carriers, propellants (present if the composition is applied as aerosol), other additives having antiperspirant and/or deodorizing effect, emulsifiers, structurants, emollients, fragrances, antioxidants and preservatives.

Liquid carriers can represent from 30% to 99%, preferably from 60% to 98% by weight of the composition. Suitable liquid carriers may be selected among water, mineral oils, silicon oils, hydrogenated polyisobutene, polydecene, paraffins, isoparaffins, aliphatic or aromatic ester oils (e.g., isopropyl myristate, lauryl myristate, isopropyl palmitate, diisopropyl sebacate, diisopropyl adipate, or C$_8$-C$_{18}$ alkyl benzoates), glycerine, polyglycol ethers, or mixtures thereof.

Propellants, if present, typically represent from 30 to 99% by weight, preferably from 50 to 95% by weight of the composition. Non-chlorinated volatile propellants are preferred, such as liquefied hydrocarbons or halogenated hydrocarbon gases (e.g., fluorinated hydrocarbons such as 1,1-difluoroethane or 1-trifluoro-2-fluoroethane). Suitable hydrocarbon gases include propane, isopropane, butane, isobutane, pentane and isopentane or mixtures thereof. Other suitable propellants include alkyl ethers, such as dimethyl ether or compressed non-reactive gasses such air, nitrogen or carbon dioxide.

Other additives having antiperspirant and/or deodorizing effect may be present at concentration from higher than 0% and up to 15% by weight of the composition. Suitable additives are aluminium or aluminium/zirconium chloride or chlorohydrate salts, such as aluminium zirconium tetrachlorohydrex gly or aluminium zirconium trichlorohydrex gly. Also suitable are sodium stearate, sodium chloride, stearyl alcohol, triclosan and zinc salts such as Zn glycinate, ZnPCA (zinc pyrrolidone carboxylate), Zn citrate, Zn gluconate, Zn phenolsulfonate, Zn ricinoleate, Zn undecylenate and Zinc coceth sulphate. The preferred further additives having antiperspirant and/or deodorizing are aluminium-free compounds.

Emulsifiers are usually present at from 0.1% to 10% by weight of the composition. Suitable emulsifiers include ceteareth-20, cetearyl glucoside, ceteth-10, ceteth-2, ceteth-20, cetyl alcohol, cocamide MEA, glyceryl laurate, glyceryl stearate and PEG-100 stearate, glyceryl stearate, glyceryl stearate SE, glycol distearate, glycol stearate, isoceteth-20, isosteareth-20, laureth-23, laureth-4, lecithin, methyl glucose sesquistearate, oleth-10/polyoxyl 10 oleyl ether NF, oleth-10, oleth-2, oleth-20, PEG-100 stearate, PEG-20 almond glycerides, PEG-20 methyl glucose sesquistearate, PEG-25 hydrogenated castor oil, PEG-30 dipolyhydroxystearate, PEG-4 dilaurate, PEG-40 sorbitan peroleate, PEG-60 almond glycerides, PEG-7 olivate, PEG-7 glyceryl cocoate, PEG-8 dioleate, PEG-8 laurate, PEG-8 oleate, PEG-80 sorbitan laurate, polysorbate 20, polysorbate 20 NF, polysorbate 60, polysorbate 60 NF, polysorbate 80, polysorbate 80 NF, polysorbate 85, PPG-11 stearyl ether, propylene glycol isostearate, sorbitan isostearate, sorbitan laurate, sorbitan monostearate NF, sorbitan oleate, sorbitan sesquioleate, sorbitan stearate and sucrose cocoate, sorbitan stearate, sorbitan trioleate, stearamide MEA, steareth-100, steareth-2, steareth-20, steareth-21 and silicone-based emusifiers.

Structurants are usually present at from 1% to 30% by weight of the composition and include hydroxy propyl cellulose, hydroxy ethyl cellulose, dibenzylidene sorbitol, sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, or propylene carbonate.

Emollients are known in the art and are used to impart a soothing effect on the skin. They may represent from 0.1 to 20% by weight of the composition. Suitable examples include PPG-14 butyl ether, PPG-15 stearyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, di-(2-ethyl hexyl)adipate, di-(2-ethyl hexyl)

succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, alkyl benzoate, hydroxyethyl stearate amide, and hydrogenated polyisobutene.

The antiperspirant and deodorant composition may include one or more fragrances. A variety of fragrances can be used in the antiperspirant and deodorant composition, if a scented product is desired. Any fragrance suitable for personal care use may be incorporated into the antiperspirant and deodorant composition. When a fragrance is used, it may be in the form of a free (non-encapsulated) fragrance, optionally emulsified, or it may be encapsulated in one of the multiple encapsulating materials used for this purpose. The fragrance is present at from 0 to 5% by weight of the composition.

Antioxidants may be present at concentration from 0.001 to 2% by weight of the compositions and include tocopherol and its derivatives, butyl hydroxyanisole (BHA), butyl hydroxytoluene (BHT), erythorbic acid, propyl gallate, sodium erythorbate, tertiary butyl hydroquinone (TBHQ), rosemary extract, ascorbic acid or mixtures thereof.

Preservatives are usually present at from 0.001 to 2% by weight of the compositions and are selected among phenoxyethanol, caprylyl glycol, ethylhexylglycerin, citric acid, benzoic acid, lactic acid or mixtures thereof.

Preferably, the deodorant and antiperspirant composition further comprise at least one of liquid carriers other than water, propellants, other additives having antiperspirant and/or deodorizing effect, emulsifiers, structurants, emollients, fragrances, antioxidants or preservatives.

EXAMPLES

Example 1

Preparation of Multi-Substituted Hydroxyapatite with Aluminium and Zinc Cations (HAP-AlZn)

A basic aqueous suspension a) of $Ca(OH)_2$ (206.7 g/l) is prepared. Said suspension is added with zinc cations ($Zn^{2+}$) derived from $ZnCO_3$ (62.8 g/l). Then an aqueous solution b) of $H_3PO_4$ (289.5 g/l) and, simultaneously, a solution c) of $AlCl_3·6H_2O$ (536.6 g/l) are added.

The addition of solutions b) and c) is carried out at a temperature of 40° C. for 3-4 hours.

After dripping the solutions b) and c) into the suspension of calcium hydroxide, added with $Zn^{2+}$ cations, the resulting mixture is left under stirring for 1 h and then to rest for 24 h. The mother liquor is then removed by centrifugation (at 6000 revolutions per minute for 20 minutes). The solid part is redispersed in distilled water and then centrifuged again. This washing operation is repeated at least three times. At the end of it, the powder is dried (by drying in a ventilated oven at 80° C.). The powder of multi-substituted hydroxyapatite thus obtained is sieved to 150 μm. The obtained multi-substituted hydroxyapatite contains $Zn^{2+}$ ions in a molar ratio Zn/Ca of 0.176 (17.6%) and $Al^{3+}$ ions in a molar ration Al/Ca of 0.264 (26.4%).

Example 2

Preparation of Cosmetic Compositions with Antiperspirant and Deodorant Properties Composition 1

A cosmetic composition with antiperspirant and deodorant properties was prepared by using 20.0% by weight of the multi-substituted hydroxyapatite with aluminium and zinc cations (HAP-AlZn) prepared in the Example 1.

The composition was prepared by using the following ingredients (reported as INCI Names except for HAP-AlZn):

Aqua, HAP-AlZn, Ethylhexyl Palmitate, Isopropyl Myristate, Cetyl alcohol, Glycerine, Olivoyl Hydrolized Wheat Protein, Cetearyl alcohol, Glyceryl stearate, Dimethicone, Leptosperum Scopiarum Oil, Phenoxyethanol, Propylene Glycol, Copaifera Officianalis Resin, Andiroba Oil, Olea Europaea Fruit Oil, Urea, Sorbitan Laurate, Benzyl Alcohol, Glucose, Sodium PCA, Hydrogenated Starch Hydrolysate, Fructose, Potassium Hydroxide, Hydrolized Wheat Protein, Dichlorobenzyl alcohol, Sodium glutamate, Glycine, Disodium EDTA, BHT, Lysine, Malic Acid, Tartaric acid, Citric Acid, Glycolic Acid, Lactic Acid, Sodium Hydroxide, Sodium Polyacrloyldimethyl taurate, Trideceth-10, Hydrogenated Polydecene, Parfum, Geraniol, 3-Methyl-4-(2,6,6-trimethyl-2-cyclohexen-1-yl)-3-buten-2-one, Coumarin, Citronellol, Hydroxycitronellal, D-Limonene, Citral, Linalool.

Composition 2 (Comparative)

A placebo control composition (not containing HAP-AlZn) was prepared by using the following ingredients (INCI Names):

Alcohol Denat., Butylene Glycol, Propylene Glycol, Aqua, Palmitic Acid, Parfum, Octyldodecanol, Stearic Acid, Sodium Hydroxide, Myristic Acid, Panthenol, Tocopheryl Acetate, Bisabolol, Pentylene Glycol, Dimethyl Phenypropanol, Menthol, Amyl Cinnamal, Benzyl Benzoate, Cinnamyl Alcohol, Citral, Citronellol, Coumarin, Eugenol, Geraniol, Hexyl Cinnamal, Hydroxycitronellal, Limonene, Linalool, Butylphenyl Methylpropional, Alpha-Isomethyl Ionone.

Example 3

Sweat Reduction Test

Compositions 1 and 2 were tested for their antiperspirant efficacy with a sweat reduction test.

The test was conducted on 16 adult subjects. Test subjects were placed in a controlled environment (temperature at 40° C. and relative humidity from 30% to 40%) to thermally induce perspiration.

Half of the subjects applied Composition 1 under left axilla and Composition 2 under right axilla, while the remaining subjects were assigned oppositely.

Underarm perspiration was evaluated at 24 hours and 48 hours after the last daily treatment. Pre-weighed absorbent pads were placed in both axillae of each test subject at the end of the warm-up period (40 minutes) in the controlled environment. Subjects remained in the controlled environment for other 20 minutes (collection period): perspiration was collected on the absorbent pads and the pads were weighed at the end of the collection period. Underarm pads were placed in a position suitable to absorb all sweat and care was taken to maintain them intact in the collection period. The quantity of each composition applied by all subjects reflected the amount that a physical personal would apply normal use conditions. In line with consumer habits subjects applied around 300 mg of product (+/−10%). The compositions were applied once daily for a treatment period of four days.

Mean perspiration (grams) of axilla of 16 subjects at 24 hours and 48 hours after the last daily treatment was calculated and the results are shown in Table 1.

TABLE 1

|  | Mean perspiration (g) | |
| --- | --- | --- |
|  | 24 hours | 48 hours |
| Composition 1 | 0.302 | 0.528 |
| Composition 2* | 0.501 | 0.790 |

*Comparative

Table 2 reports the mean sweating percent reduction for axillae treated with Composition 1 respect to axillae treated with Composition 2.

TABLE 2

| Time | Sweat reduction of Composition 1 respect to Composition 2 (%) |
| --- | --- |
| 24 hours | −35.47% |
| 48 hours | −30.46% |

As shown by the results reported in Table 1 and Table 2, Composition 1 (containing HAP-AlZn) demonstrates antiperspirant efficacy.

The invention claimed is:

1. A cosmetic composition with antiperspirant and deodorant properties comprising: from 0.05 to 35% by weight (wt %) of a multi-substituted hydroxyapatite with at least two cations selected among aluminium, zinc, magnesium, zirconium, titanium copper, silver or iron; and at least one material selected from the group consisting of: liquid carriers other than water, propellants, additives having antiperspirant and/or deodorizing effect, emulsifiers, structurants, emollients, fragrances, antioxidants, preservatives, and combinations thereof.

2. The cosmetic composition with antiperspirant and deodorant properties according to claim 1, wherein the multi-substituted hydroxyapatite is a multi-substituted hydroxyapatite with at least two cations selected from the group consisting of aluminium, zinc magnesium, and a combination thereof.

3. The cosmetic with antiperspirant and deodorant properties according to claim 1, wherein the multi-substituted hydroxyapatite is a multi-substituted hydroxyapatite with aluminium and magnesium cations.

4. The cosmetic with antiperspirant and deodorant properties according to claim 1, wherein the multi-substituted hydroxyapatite is a multi-substituted hydroxyapatite with aluminium and zinc cations.

5. The cosmetic with antiperspirant and deodorant properties according to claim 4, wherein the multi-substituted hydroxyapatite comprises $Zn^{2+}$ ions in a molar ratio Zn/Ca of from 0.2% to 35% and $Al^{3+}$ ions in a molar ratio Al/Ca of from 0.2% to 50%.

6. The cosmetic with antiperspirant and deodorant properties according to claim 4, wherein the multi-substituted hydroxyapatite comprises $Mg^{2+}$ ions in a molar ratio Mg/Ca of from 0.2% to 35% and $Zn^{2+}$ ions in a molar ratio Zn/Ca of from 0.2% to 35%.

7. The cosmetic with antiperspirant and deodorant properties according to claim 5, wherein the multi-substituted hydroxyapatite further comprises $Mg^{2+}$ ions in a molar ratio Mg/Ca of from 0.2% to 35%.

8. The cosmetic composition with antiperspirant and deodorant properties according to claim 3 wherein the multi-substituted hydroxyapatite is prepared by a process including the following steps: i) preparing a basic aqueous suspension a) of $Ca(OH)_2$, comprising zinc cations ($Zn^{2+}$); ii) simultaneously adding to the basic aqueous solution prepared in step i) an aqueous solution b) of $H_3PO_4$ and a solution c) of $AlCl_3 \cdot 6\ H_2O$.

9. A cosmetic method for reduction of perspiration of a body and/or reduction of a body odor released by the perspiration, the method comprising: applying on the skin a cosmetic composition with antiperspirant and deodorant properties comprising: from 0.05 to 35% by weight (wt %) of a multi-substituted hydroxyapatite with at least two cations selected among aluminium, zinc, magnesium, zirconium, titanium copper, silver or iron; and, at least one material selected from the group consisting of: liquid carriers other than water, propellants, additives having antiperspirant and/or deodorizing effect, emulsifiers, structurants, emollients, fragrances, antioxidants, preservatives, and combinations thereof.

10. The cosmetic method for reduction of perspiration of a body and/or reduction of a body odor released by the perspiration according to claim 9, wherein the multi-substituted hydroxyapatite is a multi-substituted hydroxyapatite with at least two cations selected from the group consisting of aluminium, zinc magnesium, and a combination thereof.

11. The cosmetic method for reduction of perspiration of a body and/or reduction of a body odor released by the perspiration according to claim 9, wherein the multi-substituted hydroxyapatite is a multi-substituted hydroxyapatite with aluminium and zinc cations.

12. The cosmetic method for reduction of perspiration of a body and/or reduction of a body odor released by the perspiration according to claim 9, wherein the multi-substituted hydroxyapatite is a multi-substituted hydroxyapatite with zinc and magnesium cations.

13. The cosmetic method for reduction of perspiration of a body and/or reduction of a body odor released by the perspiration according to claim 9, wherein the multi-substituted hydroxyapatite is a multi-substituted hydroxyapatite with aluminium and magnesium cations.

14. The cosmetic method for reduction of perspiration of a body and/or reduction of a body odor released by the perspiration according to claim 11, wherein the multi-substituted hydroxyapatite comprises $Zn^{2+}$ ions in a molar ratio Zn/Ca of from 0.2% to 35% and $Al^{3+}$ ions in a molar ratio Al/Ca of from 0.2% to 50%.

15. The cosmetic method for reduction of perspiration of a body and/or reduction of a body odor released by the perspiration according to claim 12, wherein the multi-substituted hydroxyapatite comprises $Mg^{2+}$ ions in a molar ratio Mg/Ca of from 0.2% to 35% and $Zn^{2+}$ ions in a molar ratio Zn/Ca of from 0.2% to 35%.

16. The cosmetic method for reduction of perspiration of a body and/or reduction of a body odor released by the perspiration according to claim 13, wherein the multi-substituted hydroxyapatite comprises $Mg^{2+}$ ions in a molar ratio Mg/Ca of from 0.2% to 35% and $Al^{3+}$ ions in a molar ratio Al/Ca of from 0.2% to 50%.

17. The cosmetic composition with antiperspirant and deodorant properties according to claim 11 wherein the multi-substituted hydroxyapatite is prepared by a process including the following steps: i) preparing a basic aqueous suspension a) of $Ca(OH)_2$, comprising zinc cations ($Zn^{2+}$); ii) simultaneously adding to the basic aqueous solution prepared in step i) an aqueous solution b) of $H_3PO_4$ and a solution c) of $AlCl_3 \cdot 6\ H_2O$.

* * * * *